(12) United States Patent
Wang et al.

(10) Patent No.: US 7,307,719 B2
(45) Date of Patent: Dec. 11, 2007

(54) WAVELENGTH-TUNABLE EXCITATION RADIATION AMPLIFYING STRUCTURE AND METHOD

(75) Inventors: Shih-Yuan Wang, Palo Alto, CA (US); M. Saif Islam, Mountain View, CA (US); Zhiyong Li, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 298 days.

(21) Appl. No.: 10/941,714

(22) Filed: Sep. 14, 2004

(65) Prior Publication Data

US 2006/0055920 A1    Mar. 16, 2006

(51) Int. Cl.
 *G01J 3/44* (2006.01)
 *G01J 3/45* (2006.01)
(52) U.S. Cl. .................. 356/301; 356/454; 356/519
(58) Field of Classification Search .............. 356/301, 356/454, 519
 See application file for complete search history.

(56) References Cited

U.S. PATENT DOCUMENTS

| | | | |
|---|---|---|---|
| 4,547,801 A | 10/1985 | Haisma et al. | |
| 4,674,878 A | 6/1987 | Vo-Dinh | |
| 4,802,761 A * | 2/1989 | Bowen et al. ............ | 356/301 |
| 5,017,007 A | 5/1991 | Milne et al. | |
| 5,187,461 A | 2/1993 | Brommer et al. | |
| 5,216,686 A | 6/1993 | Holm et al. | |
| 5,255,067 A | 10/1993 | Carrabba et al. | |
| 5,256,596 A | 10/1993 | Ackley et al. | |
| 5,293,392 A | 3/1994 | Shieh et al. | |
| 5,317,587 A | 5/1994 | Ackley et al. | |
| 5,335,240 A | 8/1994 | Ho et al. | |
| 5,359,618 A | 10/1994 | Lebby et al. | |
| 5,440,421 A | 8/1995 | Fan et al. | |
| 5,468,656 A | 11/1995 | Shieh et al. | |
| 5,471,180 A | 11/1995 | Brommer et al. | |
| 5,527,712 A | 6/1996 | Sheehy | |
| 5,600,483 A | 2/1997 | Fan et al. | |
| 5,609,907 A | 3/1997 | Natan | |
| 5,629,951 A * | 5/1997 | Chang-Hasnain et al. .... | 372/20 |
| 5,677,924 A | 10/1997 | Bestwick | |
| 5,682,401 A | 10/1997 | Joannopoulos et al. | |
| 5,684,817 A | 11/1997 | Houdre et al. | |
| 5,706,306 A | 1/1998 | Jiang et al. | |
| 5,739,945 A | 4/1998 | Tayebati | |
| 5,771,253 A | 6/1998 | Chang-Hasnain et al. | |
| 5,774,485 A | 6/1998 | Stein | |

(Continued)

FOREIGN PATENT DOCUMENTS

WO    WO2004/031749    4/2004

OTHER PUBLICATIONS

Martini et al., "Molecular Raman effect in the optical microcavity: QED vacuum confinement on an inelastic quantum scattering process", Physical Review A, vol. 53, No. 1, Jan. 1996.*

(Continued)

*Primary Examiner*—Gregory J. Toatley, Jr.
*Assistant Examiner*—Bryan J Giglio

(57) ABSTRACT

Wavelength-tunable radiation amplifying structures for Raman spectroscopy are disclosed that include resonant cavities having Raman signal-enhancing structures disposed therein. Systems that include the amplifying structures and methods of performing spectroscopic analysis using the structures and systems are also disclosed.

41 Claims, 9 Drawing Sheets

U.S. PATENT DOCUMENTS

| | | | |
|---|---|---|---|
| 5,784,400 | A | 7/1998 | Joannopoulos et al. |
| 5,837,552 | A | 11/1998 | Cotton et al. |
| 5,990,850 | A | 11/1999 | Brown et al. |
| 5,997,795 | A | 12/1999 | Danforth et al. |
| 5,998,298 | A | 12/1999 | Fleming et al. |
| 6,058,127 | A | 5/2000 | Joannopoulos et al. |
| 6,134,043 | A | 10/2000 | Johnson et al. |
| 6,141,360 | A | 10/2000 | Kinugawa et al. |
| 6,149,868 | A | 11/2000 | Natan et al. |
| 6,154,591 | A | 11/2000 | Kershaw |
| 6,274,293 | B1 | 8/2001 | Gupta et al. |
| 6,339,030 | B1 | 1/2002 | Constant et al. |
| 6,396,083 | B1 | 5/2002 | Ortiz et al. |
| 6,406,777 | B1 | 6/2002 | Boss et al. |
| 6,434,180 | B1 | 8/2002 | Cunningham |
| 6,525,880 | B2 | 2/2003 | Flanders et al. |
| 6,546,029 | B2 | 4/2003 | Sirbu et al. |
| 6,608,685 | B2 | 8/2003 | Wood et al. |
| 6,608,716 | B1 | 8/2003 | Armstrong et al. |
| 6,623,977 | B1 | 9/2003 | Farquharson et al. |
| 6,649,683 | B2 | 11/2003 | Bell |
| 6,650,675 | B2 | 11/2003 | Sahara et al. |
| 6,678,289 | B2 | 1/2004 | Kim |
| 6,700,910 | B1 | 3/2004 | Aoki et al. |
| 6,711,200 | B1 | 3/2004 | Scherer et al. |
| 6,867,900 | B2 * | 3/2005 | Weisbuch et al. ............ 359/321 |
| 7,177,021 | B2 * | 2/2007 | Wang et al. ................. 356/301 |
| 2002/0142480 | A1 | 10/2002 | Natan |
| 2002/0182716 | A1 * | 12/2002 | Weisbuch et al. ......... 435/287.2 |
| 2003/0120137 | A1 | 6/2003 | Pawluczyk |
| 2004/0063214 | A1 * | 4/2004 | Berlin et al. ................... 436/94 |
| 2004/0120380 | A1 | 6/2004 | Kim et al. |
| 2004/0142484 | A1 * | 7/2004 | Berlin et al. ................. 436/171 |
| 2004/0150818 | A1 | 8/2004 | Armstrong et al. |
| 2004/0174521 | A1 * | 9/2004 | Drachev et al. ............ 356/301 |

OTHER PUBLICATIONS

Kottmann, J. P. and Martin, O. J. F., "Plasmon resonances of silver nanowires with a nonregular cross section", Physical Review B, vol. 64, 235402, Nov. 2001.*

Blanco, Alvaro, et al., "Large-scale synthesis of a silicon photonic crystal with a complete three-dimensional bandgap near 1.5 micrometres," Letters to Nature, Nature, vol. 405, May 25, 2000, pp. 437-440.

Campbell, M., et al., "Fabrication of photonic crystals for the visible spectrum by holographic lithography," Letters to Nature, Nature, vol. 404, Mar. 2, 2000, pp. 53-56.

Chang-Hasnain, Connie J., "Tunable VCSEL," IEEE Journal on Selected Topics in Quantum Electronics, vol. 6, No. 6, Nov./Dec. 2000, pp. 978-987.

Emory, Steven R., et al., "Screening and Enrichment of Metal Nanoparticles with Novel Optical Properties," J. Phys. Chem. B, 1998, 102, pp. 493-497.

Joannopoulos, J.D., et al., "Photonic crystals: putting a new twist on light," Nature, vol. 386, Mar. 13, 1997, pp. 143-149.

Johnson, Steven G., et al., Introduction to Photonic Crystals: Block's Theorem, Band Diagrams, and Gaps (But No Defects), Feb. 3, 2003, pp. 1-16.

Kneipp, Katrin, et al., Single Molecule Detection Using Surface-Enhanced Raman Scattering (SERS), Physical Review Letters, vol. 78, No. 9, Mar. 3, 1997, pp. 1667-1670.

Lalanne, Ph., et al., "Two physical mechanisms for boosting the quality factor to cavity volume ratio of photonic crystal microcavities," Optics Express, Feb. 9, 2004, vol. 12, No. 3, pp. 458-467.

Michaels, Amy M., et al., "Surface Enhanced Raman Spectroscopy of Individual Rhodamine 6G Molecules on Large Ag Nanocrystals," J. Am. Chem. Soc., 1999, 121, pp. 9932-9939.

Qi, Minghao, et al., "A three-dimensional optical photonic crystal with designed point defects," Letters to Nature, Nature, vol. 429, Jun. 3, 2004, pp. 538-542.

Tao, Andrea, et al., "Langmuir-Blodgett Silver Nanowire Momolayers for Molecular Sensing Using Surface-Enhanced Raman Spectroscopy," Nano Letters, vol. 3, No. 9, 2003, pp. 1229-1233.

Vlasov, Yuril A., et al., "On-chip natural assembly of silicon photonic bandgap crystals," Letters to Nature, Nature, vol. 414, Nov. 15, 2001, pp. 289-293.

Cairo F et al-"QED-Vacuum Confinement of Inelastic Quantum Scattering at Optical Frequencies: A New Perspective in Raman Spectroscopy"-Phys Rev Letts-vol. 70 No. 10-Mar. 9, 1999.

Fainstein A et al-"Raman Scattering Enhancement by Optical Confinement in a Semiconductor Planar Microcavity"-Phys Rev Letts-vol. 75 No. 20- Nov. 13, 1995-pp. 3764-3767.

Tuan, Vo-Dihn-"Surface-Anhanced Raman Spectroscopy Using Metallic Nanostructures"-Trends in Analytical Chemistry-vol. 17 No. 8-9 1998-pp. 557-582.

* cited by examiner

WAVELENGTH-TUNABLE EXCITATION RADIATION AMPLIFYING STRUCTURE AND METHOD

FIELD OF THE INVENTION

The present invention relates to Raman spectroscopy chemical analysis. More particularly, the present invention relates to devices, systems, and methods for increasing the intensity of excitation radiation of varying wavelengths in surface-enhanced Raman spectroscopy (SERS).

BACKGROUND OF THE INVENTION

Raman spectroscopy is a well-known spectroscopic technique for performing chemical analysis. In conventional Raman spectroscopy, high intensity monochromatic light provided by a light source, such as a laser, is directed onto an analyte (or sample) that is to be chemically analyzed. The analyte may contain a single molecular species or mixtures of different molecular species. Furthermore, Raman spectroscopy may be performed on a number of different types of molecular configurations, such as organic and inorganic molecules in either crystalline or amorphous states.

The majority of the incident photons of the radiation are elastically scattered by the analyte molecule. In other words, the scattered photons have the same frequency, and thus the same energy, as the photons that were incident on the analyte. However, a small fraction of the photons (i.e., 1 in $10^7$ photons) are inelastically scattered by the analyte molecule. These inelastically scattered photons have a different frequency than the incident photons. This inelastic scattering of photons is termed the "Raman effect." The inelastically scattered photons may have frequencies greater than, or, more typically, less than the frequency of the incident photons. When an incident photon collides with a molecule, energy may be transferred from the photon to the molecule or from the molecule to the photon. When energy is transferred from the photon to the molecule, the scattered photon will then emerge from the sample having a lower energy and a corresponding lower frequency. These lower-energy Raman scattered photons are commonly referred to in Raman spectroscopy as the "Stokes radiation." A small fraction of the analyte molecules are already in an energetically excited state. When an incident photon collides with an excited molecule, energy may be transferred from the molecule to the photon, which will then emerge from the sample having a higher energy and a corresponding higher frequency. These higher-energy Raman scattered photons are commonly referred to in Raman spectroscopy as the "anti-Stokes radiation."

The Stokes and the anti-Stokes radiation is detected by a detector, such as a photomultiplier or a wavelength-dispersive spectrometer, which coverts the energy of the impinging photons into an electrical signal. The characteristics of the electrical signal are at least partially a function of the energy (or wavelength, frequency, wave number, etc.) of the impinging photons and the number of the impinging photons (intensity). The electrical signal generated by the detector can be used to produce a spectral graph of intensity as a function of frequency for the detected Raman signal (i.e., the Stokes and anti-Stokes radiation). By plotting the frequency of the inelastically scattered Raman photons against intensity, a unique Raman spectrum is obtained, which corresponds to the particular analyte. This Raman spectrum may be used for many purposes, such as identifying chemical species, identifying chemical states or bonding of atoms and molecules, and even determining physical and chemical properties of the analyte.

Since the intensity of the Raman scattered photons is low, very intense laser light sources are usually employed to provide the excitation radiation. Another Raman spectroscopy technique called Surface Enhanced Raman Spectroscopy (SERS) has been developed to increase the Raman signal produced by an analyte and to allow surface studies of the analyte. In SERS, the analyte molecules are adsorbed onto or positioned near a specially roughened metal surface. Typically, the metal surface is made from gold, silver, copper, platinum, palladium, aluminum, or other metals or metal alloys. SERS has also been performed employing metallic nanoparticles or nanowires for the metal surface, as opposed to a roughened metallic surface. The intensity of the Raman scattered photons from a molecule adsorbed on such a metal surface is typically about $10^4$-$10^6$ greater than conventional Raman Spectroscopy and can be as high as $10^8$-$10^{14}$. In other words, more photons are inelastically scattered by the analyte molecules in SERS compared to conventional Raman spectroscopy.

The surface enhancement of the Raman signal in SERS is currently attributed to two primary mechanisms: electromagnetic field enhancement and chemical enhancement, electromagnetic field enhancement being the dominant mechanism. The enhancement of the Raman signal is at least partially dependent on the surface roughness or surface features of the metal surface. In SERS, a strong electromagnetic field is present in the areas adjacent to and near the metallic surface, which is experienced by the analyte. This strong electromagnetic field enhances the Raman signal emitted from the analyte, which is, at least in part, proportional to the square of the enhanced electromagnetic field. Thus, SERS may be used to perform, for example, surface studies and studies of monolayers of materials adsorbed on metals. While SERS is an effective chemical analysis tool, it requires rather large and powerful laser light sources. A typical SERS system occupies a large table and is not particularly portable.

Accordingly, there is a need for a more compact and portable SERS system. There is also a need for a light source that requires less power during operation that also will enhance, simultaneously, the intensity of the Raman signal to enable more sensitive chemical analysis.

BRIEF SUMMARY OF THE INVENTION

A wavelength-tunable excitation radiation amplifying structure comprises: a support structure; a first material layer attached to the support structure having a face; a second material layer having a first portion attached to the support structure and a second portion having a first surface and a second surface, the second surface being generally parallel to the first surface, the second surface opposing the face of the first material layer and separated therefrom by a distance; means for displacing the second portion of the second material layer relative to the face of the first material layer to change the distance therebetween; and at least a part of a Raman signal-enhancing structure disposed between the face of the first material layer and the second surface of the second portion of the second material layer.

A wavelength tunable excitation radiation amplifying structure as discussed above wherein the means for displacing the second portion of the second material layer relative to the face of the first material layer include a first electrical contact disposed on the first material layer and a second electrical contact disposed on the second material layer, whereby a voltage applied between the first electrical contact and the second electrical contact causes the distance between the first material layer and the second material layer to change.

A spectroscopic analysis system includes a radiation source for emitting excitation radiation, a wavelength-tunable excitation radiation amplifying structure, and a detector configured to receive radiation emitted from the analyte when the analyte is subjected to excitation radiation emitted from the source.

A method of performing surface enhanced Raman spectroscopy (SERS) comprises the steps of: providing a wavelength-tunable excitation radiation amplifying structure including: a support structure; a first material layer attached to the support structure having a face; a second material layer having a first portion attached to the support structure and a second portion having a first surface and a second surface, the second surface being generally parallel to the first surface, the second surface opposing the face of the first material layer and separated therefrom by a distance; a first electrical contact disposed on the first material layer; a second electrical contact disposed on the second material layer, whereby a voltage applied between the first electrical contact and the second electrical contact causes the distance between the first material layer and the second portion of the second material layer to change; and at least a portion of a Raman signal-enhancing structure disposed between the face of the first material layer and the second surface of the second portion of the second material layer; providing an analyte disposed proximate the Raman signal-enhancing structure; irradiating a surface of the wavelength-tunable excitation radiation amplifying structure with excitation radiation; and tuning the wavelength-tunable excitation radiation amplifying structure by applying a voltage between the first electrical contact and the second electrical contact and changing the voltage until the excitation radiation is amplified.

A wavelength-tunable excitation radiation amplifying structure comprises a metallic nanostructure disposed within a wavelength-tunable resonant cavity.

BRIEF DESCRIPTION OF THE SEVERAL VIEWS OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE INVENTION

The present invention, in a number of embodiments, includes structures that increase or amplify the intensity of excitation radiation in surface enhanced Raman spectroscopy (SERS), systems that include such structures, and methods of using the same. The structures include wavelength-tunable resonant cavities. The term "amplify" is used in its broadest sense herein as meaning to increase or make greater, such as increasing the intensity of radiation within a cavity.

Structures having Fabry-Perot resonant cavities therein, or cavities formed in photonic crystals therein, can be used to increase the intensity of radiation. A SERS sample to be analyzed (referred to herein as an "analyte") may be positioned within one of these cavities to subject it to the amplified radiation. Fabry-Perot resonant cavities and cavities formed in photonic crystals may amplify radiation of only specific wavelengths, which are at least partly determined by the physical dimensions of the resonant cavity. Lasers, which typically are used as the source for the excitation radiation, often emit radiation at a fixed wavelength. If the wavelength of the excitation radiation is not a wavelength that will resonate within the cavity (i.e., the wavelength does not correspond to a resonant mode of the cavity), the intensity of the radiation may not be increased within the cavity. Additionally, because of the very small size of these resonant cavities, it is very difficult to fabricate a cavity having the precise dimensions required such that a pre-selected wavelength will resonate and be amplified within the cavity.

The radiation amplifying structures disclosed herein include wavelength-tunable amplifying structures having means for changing the wavelengths of radiation that may resonate within the cavity. Therefore, a user can tune the cavity to resonate the precise wavelength of the incident excitation radiation being used.

Figure 1A:
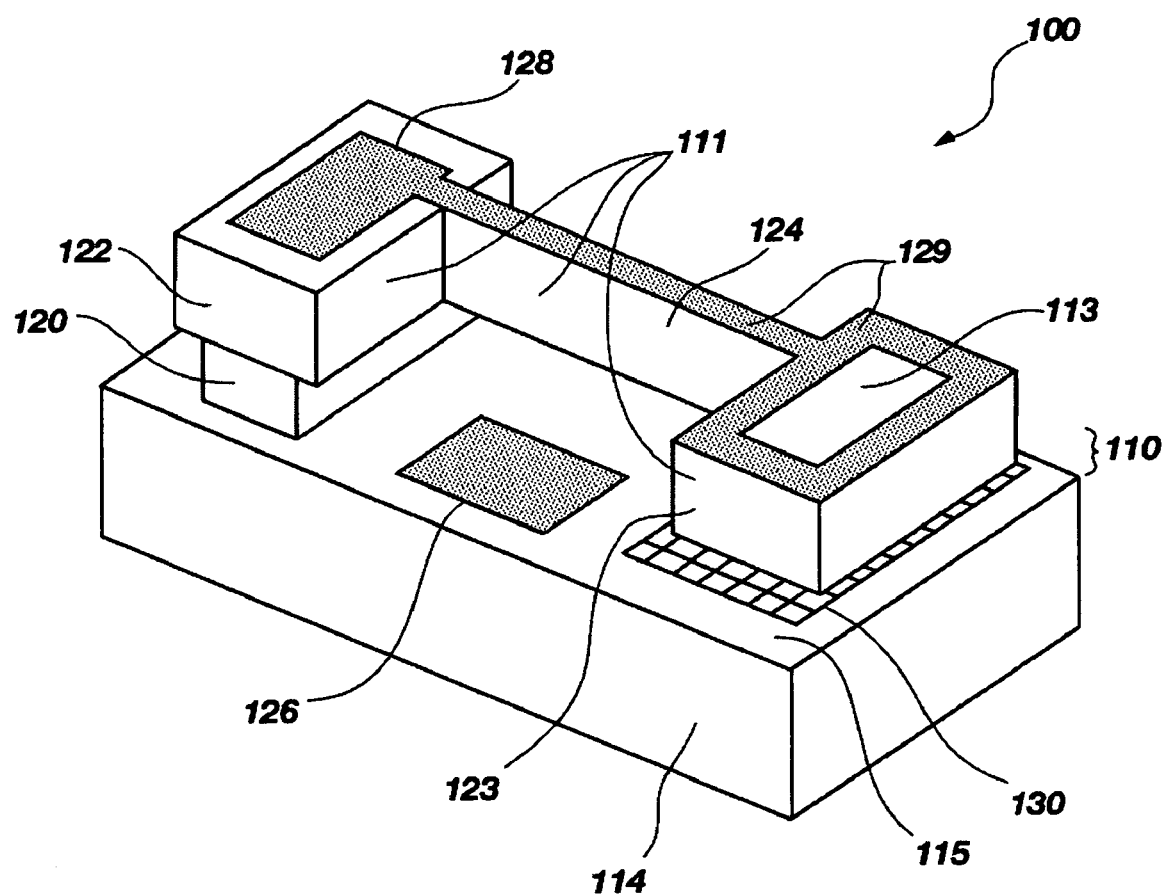
FIG. 1A is a perspective view of an apparatus having a single-arm cantilever according to one embodiment of the invention.
Figure 1B:
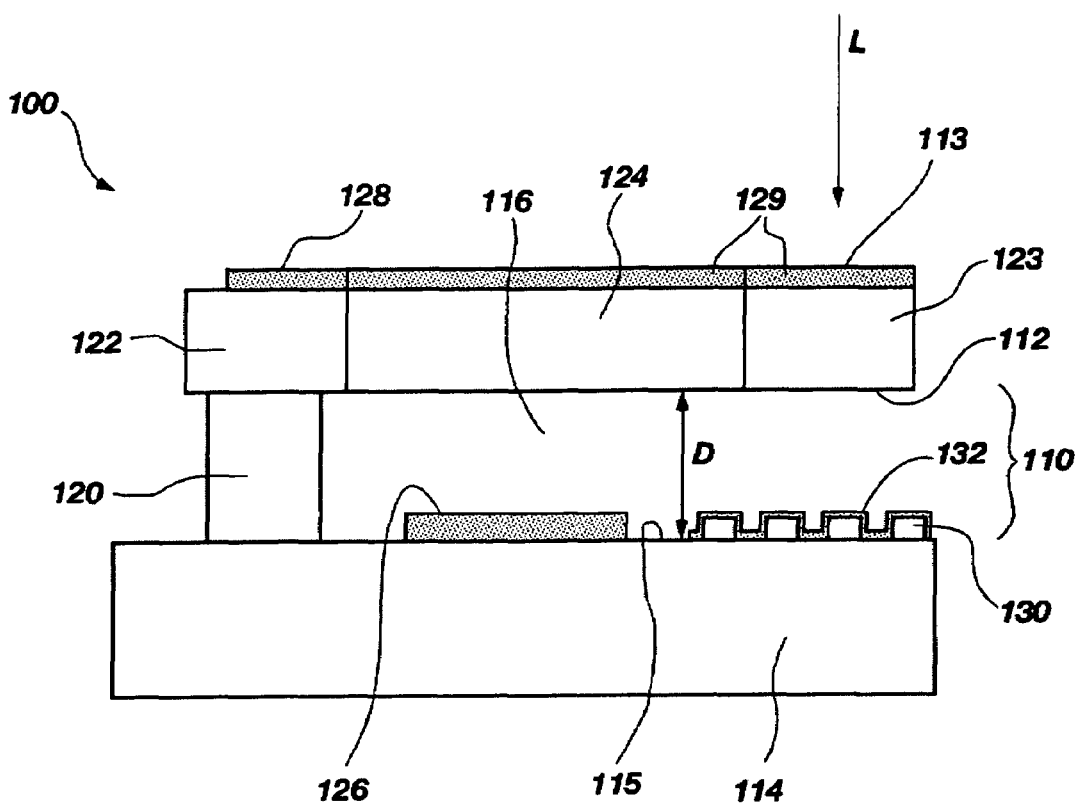
FIG. 1B is a side view of the apparatus of FIG. 1A.

A perspective view of a first exemplary embodiment of the invention is shown in FIGS. 1A and 1B. A wavelength-tunable radiation amplifying structure 100 includes an upper material layer 111 and a lower material layer 114 separated by a distance D. An insulating support member 120 may be disposed between at least a portion of the upper material layer 111 and at least a portion of the lower material layer 114, and an air gap 116 may be provided between the remaining portions. A resonant cavity 110 is defined between the upper material layer 111 and the lower material layer 114, and may include at least a portion of the air gap 116. A Raman signal-enhancing structure 130 may be disposed between the upper material layer 111 and the lower material layer 114 within the resonant cavity 110.

The upper material layer 111 may include a first portion, or cantilever base member 122, and a second portion 123. A cantilever arm 124 may extend laterally between the cantilever base member 122 and the second portion 123, supporting the second portion 123 of the upper material layer 111 vertically above the lower material layer 114. The cantilever base member 122, the cantilever arm 124, and the second portion 123 may be formed as a monolithic layer or member. The second portion 123 of the upper material layer 111 may include a lower surface 112 (FIG. 1B) and an upper surface 113 that are generally parallel to each other. The cantilever base member 122 may be attached to a surface of an insulating support structure 120.

The lower material layer 114 may include a face 115 opposing the lower surface 112 of the upper material layer 111 and may be separated therefrom by the distance D (FIG. 1B). The lower material layer 114 also may be attached to an surface of the insulating support structure 120 such that a portion of the lower material layer 114 extends laterally to be positioned below the second portion 123 of the upper material layer 111.

Upper material layer 111 and lower material layer 114 can be made from any material, at least a portion of which may include conductive or semiconductive material such as silicon doped with phosphorous or aluminum. Insulating support structure 120 can be formed from any nonconductive material including, but not limited to, silicon dioxide or epoxy. At least a portion of upper material layer 111 and lower material layer 114 should be at least partially transparent to the incident excitation radiation used in the SERS system.

An upper electrical contact 128 is disposed on the cantilever base member 122 and is electrically continuous with a conductive runner 129 that extends along the top surface of the cantilever arm 124 and onto at least a portion second portion 123 of the upper material layer 111. The conductive runner 129 ensures electrical conductivity between the upper electrical contact 128 and the second portion 123 of the upper material layer 111. A lower electrical contact 126 is disposed on the lower material layer 114. The upper electrical contact 128 and the lower electrical contact 126 may be located anywhere on the cantilever base member 122 and the lower material layer 114 respectively. Lower electrical contact 126, upper electrical contact 128, and conductive runner 129 can be formed from any conductive material including, but not limited to, gold, copper, platinum, silver, and other metals and alloys.

With continuing reference to FIGS. 1A and 1B, the Raman signal-enhancing structure 130 located within the resonant cavity 110 is used to enhance the Raman signal produced by photons that are inelastically scattered by the analyte 132 during analysis. The Raman signal-enhancing structure 130 may be used to effect electromagnetic enhancement of the Raman signal, chemical enhancement of the Raman signal, or both. As used herein, the term "Raman signal-enhancing structure" means any structure configured and formed of a material that may produce enhancement of the Raman signal. The representative Raman signal-enhancing structure 130 illustrated in FIGS. 1A and 1B may include a mesh or screen formed from metallic rods or wires having a diameter preferably less than about 20 nanometers. Alternative Raman signal-enhancing structures include, but are not limited to, arbitrarily and selectively arranged particles, dots, columns, rods, columns, pyramids, or any other shape or structure that is capable of enhancing the Raman signal produced by atoms or molecules adsorbed thereon or positioned near thereto, including a simple roughened metal surface.

Exemplary materials for the Raman signal-enhancing structure 130 include, but are not limited to, gold, silver, copper, aluminum, chromium, platinum, palladium, or any other material capable of enhancing the Raman signal produced by atoms or molecules adsorbed on or positioned near the Raman signal-enhancing structure 130. Although the materials that form the Raman signal-enhancing structure 130 typically are not transparent to the wavelengths of radiation used in Raman spectroscopy (about 350 nm to about 1000 nm), the Raman signal-enhancing structure may be formed with apertures or spaces therethrough (such as the apertures through a screen or mesh) to allow radiation to pass through the Raman signal-enhancing structure. In addition, chemical receptors, or chemical species that interact both with the Raman signal-enhancing structure 130 and the analyte 132 may be provided during operation as known in the art either to promote binding of the analyte 132 to the Raman signal-enhancing structure 130, or to enhance detection of the analyte 132.

The Raman signal-enhancing structure 130 may be located at any position within the wavelength-tunable resonant cavity 110. To position the Raman signal-enhancing structure 130 vertically within the wavelength-tunable resonant cavity 110, it may be supported by an insulating support structure (not shown) similar to insulating support structure 120 within the resonant cavity 110. The Raman signal-enhancing structure 130 may be bonded to the face 115 of the lower material layer 114 or merely disposed thereon.

The overall size of the radiation amplifying structure 100 is not critical. However, the distance D, shown in FIG. 1B, may be between about 0.1 microns and about 2 microns when the second portion 123 of the upper material layer 111 is in a non-deflected state. In addition, the dimensions of the cantilever arm 124 must be tailored to provide stability of the upper material layer 111, while allowing for appropriate deflection thereof when the resonant cavity 110 is being tuned to amplify the excitation radiation, as described subsequently herein.

All features of the Radiation amplifying structure 100 may be formed using conventional microelectronic fabrication techniques on a support substrate such as, for example, a silicon wafer, partial wafer, or a glass substrate. Examples of techniques for depositing material layers include, but are not limited to, molecular beam epitaxy (MBE), atomic layer deposition (ALD), chemical vapor deposition (CVD), physical vapor deposition (PVD), sputter deposition and other known microelectronic layer deposition techniques. Photolithography may be used, for example, to pattern features in layers of the device as they are being formed. Examples of techniques that can be used for selectively removing portions of the layers include, but are not limited to, wet etching, dry etching, plasma etching, and other known microelectronic etching techniques. These techniques are known in the art and will not be further described herein.

The operation of the radiation amplifying structure 100 can be described with reference to FIGS. 1A and 1B. The wavelength-tunable resonant cavity 110 may function as Fabry-Perot cavity to increase the intensity of excitation radiation. A simple Fabry-Perot resonator may include two parallel, flat, material layers. Upper material layer 111 and lower material layer 114 function as the material layers of a Fabry-Perot resonator. A resonant cavity 110 is provided by a portion of the air gap 116 between the second portion 123 of the upper material layer 111 and the lower material layer 114. The material layers may have a refractive index (or dielectric constant) different than that of the gap 116. When excitation radiation impinges on the upper surface 113 of the upper material layer 111 in the direction illustrated by direction arrow L (FIG. 1B), some of the radiation may pass through the upper material layer 111 into the resonant cavity 110. The change in refractive index at the interface between the lower surface 112 of the second portion 123 of the upper material layer 111 and the air gap 116, and at the interface between the face 115 of the lower material layer 114 and the air gap 116, may cause some of the radiation to be reflected internally within the resonant cavity 110 between the lower surface 112 and the face 115 rather than being transmitted through the one of the material layers. When the distance D separating the lower surface 112 of the upper material layer 111 and the opposing face 115 of the lower material layer 114 is equal to an integer number of half wavelengths of the excitation radiation, the excitation radiation may interfere constructively, causing amplification of the intensity of the radiation inside the resonant cavity 110.

The intensity of the incident excitation radiation may be amplified within the resonant cavity 110 by a factor of about 1000. Therefore, as an example, if the power of the excitation radiation source 152 is 1 mW, the power of the amplified radiation 154 resonating within the resonant cavity 110 may be about 1 W.

When the distance D is not equal to an integer number of half wavelengths of the excitation radiation, the internally reflected radiation may interfere destructively, causing the intensity of the excitation radiation inside the cavity to be diminished, which may render the radiation amplifying structure ineffective for performing SERS.

Figure 2A:
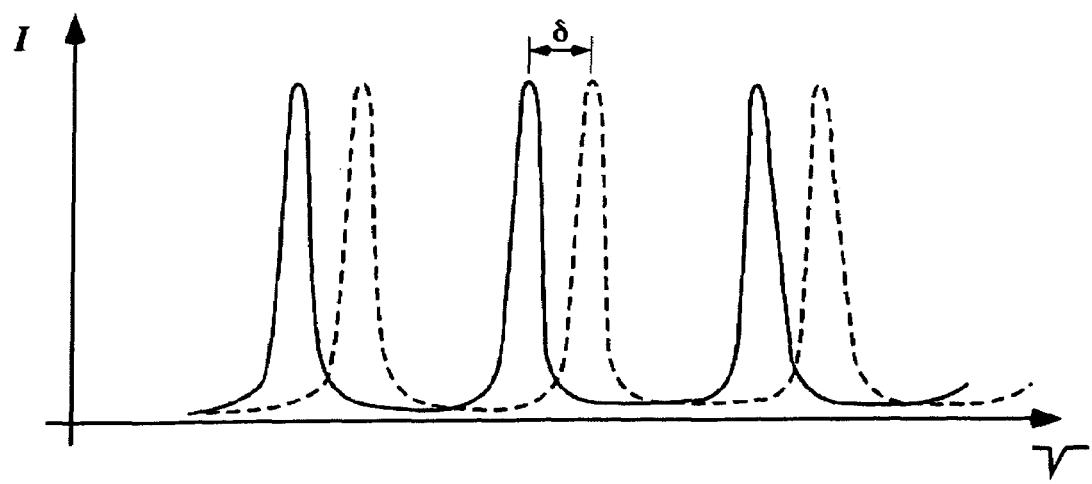
FIG. 2A is a graph that illustrates the intensity of radiation within a resonant cavity as a function of the wavelength of the incident radiation for a Fabry-Perot optical resonator, and the shift δ in resonating frequencies that can be achieved using a tunable resonant cavity according to the invention.

A graph of intensity of the excitation radiation within the resonant cavity 110 as a function of the frequency of the incident excitation radiation will have a series of peaks corresponding to the resonant frequencies (resonant modes) of the cavity, similar to that shown by the solid lines in FIG. 2A. When the distance D separating the lower surface 112 and the opposing face 115 is not an integer multiple of half the wavelength of the excitation radiation, and the radiation is not amplified within the resonant cavity 110, a voltage may be applied between lower electrical contact 126 and upper electrical contact 128. The lower electrical contact 126 and upper electrical contact 128 are electrically continuous with the second portion 123 of the upper material layer 111 and with the lower material layer 114 respectively, which may be formed from semiconductive materials, such as doped silicon for example. As a result, opposite charges may accumulate within the upper material layer 111 and the lower material layer 114. Because the charges are opposite, an attractive electrostatic force is applied to upper material layer 111 and lower material layer 114, causing cantilever arm 124 to bend downwards towards lower material layer 114. The distance D separating the lower surface 112 of the upper material layer 111 and the opposing face 115 of the lower material layer 114 may thereby be adjusted until the distance D is equal to an integer number of half wavelengths of the excitation radiation, thereby tuning the resonant cavity 110 to the wavelength of the excitation radiation and causing amplification of the excitation radiation within the resonant cavity 110.

The effect of tuning the cavity on the resonant frequencies or modes is illustrated in FIG. 2A. By changing the distance D, the peaks of the resonating frequencies are shifted by a factor δ, resulting in a spectrum illustrated by the dashed lines. Thus, the voltage may be adjusted until one of the resonating frequencies or peaks on the plot is aligned with the frequency of the excitation radiation. If the excitation radiation source includes a wavelength-tunable laser, both the wavelength of the laser and the resonating frequency of the cavity may be adjusted to provide a greater range of tunability.

Some of the photons of the amplified radiation within the cavity will be inelastically scattered by the analyte atoms and molecules as Stokes and Anti-Stokes Raman radiation, which may be detected by a detector. The Stokes and Anti-Stokes radiation may be scattered in all directions and may be detected at any angle relative to directional arrow L shown in FIG. 1B. However, the scattered Raman signal is often detected from a direction orthogonal to the incident excitation radiation to minimize the signal from excitation radiation not scattered, or scattered elastically, by the analyte.

A reflective coating may also be provided on the lower surface 112 of the second portion 123 of the upper material layer 111, and on the opposing face 115 of the lower material layer 114. Reflective coatings may be made from silver, diamond, or any other material that will at least partially reflect the incident radiation. The reflective coatings may cause more of the radiation to reflect internally inside the cavity, instead of being transmitted through the material layers, thereby further increasing the intensity of the radiation inside the cavity.

Figure 3:
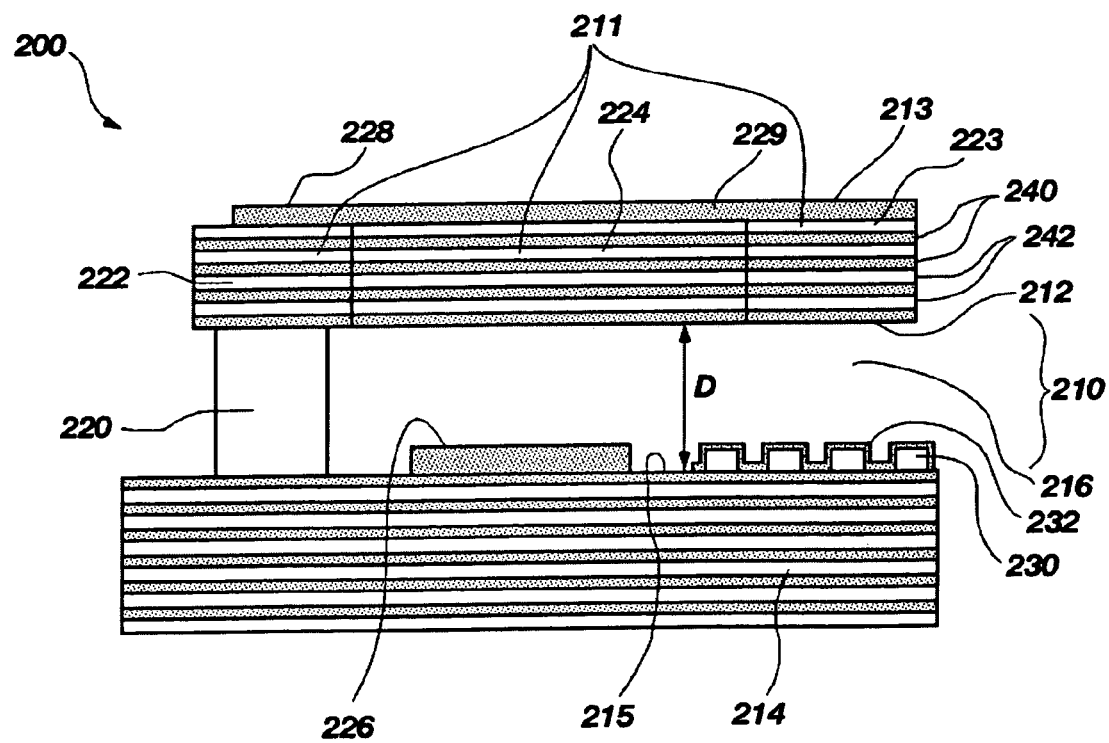
FIG. 3 is a perspective view of an exemplary apparatus of the invention comprising distributed Bragg reflectors.

A second exemplary embodiment of the invention is shown in FIG. 3. A wavelength-tunable radiation amplifying structure 200 may include an upper material layer 211 and a lower material layer 214 separated by a distance D. An insulating support member 220 may be disposed between at least a portion of the upper material layer 211 and at least a portion of the lower material layer 214, and an air gap 216 may be provided between the remaining portions. A resonant cavity 210 is defined between the upper material layer 211 and the lower material layer 214, and may include at least a portion of the air gap 216. A Raman signal-enhancing structure 230 may be disposed between the upper material layer 211 and the lower material layer 214 within the resonant cavity 210.

The upper material layer 211 may include a first portion, or cantilever base member 222, and a second portion 223. A cantilever arm 224 extends laterally between the cantilever base member 222 and the second portion 223, supporting the second portion 223 of the upper material layer 211 vertically above the lower material layer 214. The upper material layer 211, cantilever arm 224, and the cantilever base member 222 may be formed as a monolithic layer or member. The second portion 223 of the upper material layer 211 includes a lower surface 212 and an upper surface 213 that are generally parallel to each other. The cantilever base member 222 may be attached to a surface of the insulating support structure 220.

The lower material layer 214 may include a face 215 opposing the lower surface 212, and may be separated therefrom by a distance D. The lower material layer 214 also may be attached to an opposite surface of the insulating support structure 220 with a portion of the lower material layer 214 extending laterally to be positioned below the second portion 223 of the upper material layer 211.

An upper electrical contact 228 is disposed on the cantilever base member 222 and is electrically continuous with a conductive runner 229 that extends along the top surface of the cantilever arm 224 and onto at least a portion second portion 223 of the upper material layer 211. The conductive runner 229 ensures electrical conductivity between the upper electrical contact 228 and the second portion 223 of the upper material layer 211. A lower electrical contact 226 is disposed on the lower material layer 214. The upper electrical contact 228 and the lower electrical contact 226 may be located anywhere on the cantilever base member 222 and the lower material layer 214 respectively. Lower electrical contact 226, upper electrical contact 228, and conductive runner 229 can be formed from any conductive material including, but not limited to, gold, copper, platinum, silver, and other metals and alloys.

The Raman signal-enhancing structure 230 located within the resonant cavity 210 is used to enhance the Raman signal produced by photons that are inelastically scattered by the analyte 232 during analysis. The exemplary Raman signal-enhancing structure 230 illustrated in FIG. 3 includes an array of vertical columns preferably having a diameter less than about 20 nanometers. The Raman signal-enhancing structure 230 may be identical to the Raman signal-enhancing structure 130 (discussed previously in relation to the radiation amplifying structure 100 of FIG. 1) in all other respects.

Upper material layer 211 and lower material layer 214 each may include Bragg mirrors (distributed Bragg reflectors or DBR's), which may be used as reflective mirrors in Fabry-Perot resonators. Bragg mirrors are highly reflective structures and may have a reflectivity as high as about 99.99%. Bragg mirrors include a multilayer stack of alternating films of high and low refractive index material, shown in FIG. 3 as low-index films 240 and high-index films 242. Reflectivity generally increases with the number of pairs of alternating films. In the illustrated embodiment, the upper material layer 211 includes four pairs of films and the lower material layer 214 includes six pairs of films. However, the upper material layer 211 and lower material layer 214 may include from one to about 60 pairs of films, and each layer may comprise an equal or unequal number of films as the other layer.

The thickness of each low-index film 240 and each high-index film 242 may be selected to be approximately one-fourth the wavelength of the excitation radiation divided by the refractive index of the material from which the film is formed ($\lambda/4\, n_{ri}$, where $\lambda$ is the wavelength of the incident radiation and $n_{ri}$ is the refractive index of the material).

Surface enhanced Raman spectroscopy is typically performed using excitation radiation at wavelengths between about 350 nanometers and about 1000 nanometers. Therefore, as an example, if the excitation radiation of a SERS system were to have a wavelength of 800 nanometers, and the refractive index of the low-index films 240 and the high-index films 242 were 2, the thickness of the low-index films 240 and the high-index films 242 may be approximately 100 nanometers. In this configuration, the total thickness of the lower material layer 214 would be approximately 1200 nanometers (12 films each having a thickness of 100 nm), the total thickness of the upper material layer 211 would be approximately 800 nanometers, and the distance D could be selected to be 400 nm, 1200 nm, 1600 nm, 2000 nm, 8000 nm, etc. (i.e., any integer multiple of one half of 800 nm).

The low-index films 240 and the high-index films 242 of the Bragg mirrors may be formed from a variety of materials. As an example, the high-index films 242 may be formed from GaAs and the low-index films 240 of AlGaAs. Other examples of suitable material combinations for low-index films 240 and high-index films 242 include, but are not limited to: AlGaAs films having alternating atomic percents of Al and Ga; GaN and GaAlN; and GaInAsP and InP. Many such suitable material pairs are known in the art and are intended to be included within the scope of the invention.

The resonant cavity 210 defined by the lower material layer 214 and the upper material layer 211 of the radiation amplifying structure 200 may include a Fabry-Perot resonant cavity, and may operate in the same manner described previously in relation to the radiation amplifying structure 100 of FIG. 1.

Bragg mirrors are one-dimensional photonic crystals. Photonic crystals are formed by dispersing a material of one refractive index (or dielectric constant) periodically within a matrix having a different refractive index (or dielectric constant). A one-dimensional photonic crystal is a three-dimensional structure that exhibits periodicity in refractive index in one dimension. Bragg mirrors are an example of a one-dimensional photonic crystal. The alternating thin films have different refractive indices. The combination of several thin films forms a three-dimensional structure that exhibits periodicity in refractive index in directions other than parallel to the planes of the thin films.

A two-dimensional photonic crystal may be formed by periodically dispersing rods, columns, or fibers of a first material having a first refractive index within a matrix of a second material having a second, different refractive index. Two-dimensional photonic crystals exhibit periodicity in only two dimensions, (i.e., the directions perpendicular to the length of the rods or columns), but no periodicity is exhibited in directions parallel to the length of the columns.

Finally, a three-dimensional photonic crystal may be formed by periodically dispersing small spheres or other spatially confined areas of a first material having a first refractive index within a matrix of a second material having a second, different refractive index. Three-dimensional photonic crystals may exhibit periodicity in refractive index in all directions within the crystal.

Figure 2B:
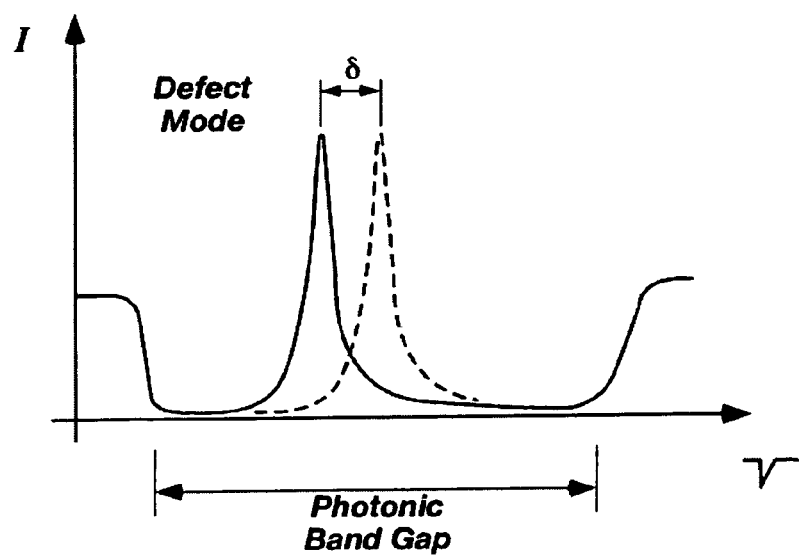
FIG. 2B is a graph that illustrates the intensity of radiation within a resonant cavity as a function of the wavelength of the incident radiation for a defect mode associated with a defect resonant cavity in a photonic crystal, and the shift δ in resonating frequencies that can be achieved using a tunable resonant cavity according to the invention.

Photonic crystals may exhibit a photonic bandgap over a range of certain frequencies in the directions exhibiting periodicity in refractive index (see FIG. 2B). In other words, there is a range of frequencies of radiation that will not be transmitted through the crystal in the directions exhibiting periodicity in refractive index. This range of frequencies that are not transmitted is known as the photonic bandgap of the photonic crystal. No photonic bandgap may be exhibited in directions that do not exhibit periodicity in refractive index.

When the periodicity in refractive index in a photonic crystal is interrupted, perhaps by a defect or a missing film in a Bragg mirror, certain defect modes may be generated. A defect may be generated within a photonic crystal by, for example, changing the refractive index within the crystal at a specific location, changing the size of a feature in the crystal, or by removing one feature from the periodic array within the crystal. Defect modes allow certain frequencies of radiation within the bandgap to be partially transmitted through the crystal and enter into the defect area where the photons of the radiation are at least partially trapped or confined. As more photons enter the defect and become trapped or confined, the radiation intensity may be increased within the cavity, providing a similar intensity amplifying effect as that produced by a Fabry-Perot resonant cavity (FIG. 2B). The frequencies associated with the defect modes are, at least partially, a function of the dimensions of the defect. The finite-difference time-domain method may be used to solve the full-vector time-dependent Maxwell's equations on a computational grid including the macroscopic dielectric function, which will be at least partially a function of the feature dimensions, and corresponding dielectric constant within those features, of the photonic crystal to determine which wavelengths may be forbidden to exist within the interior of any given crystal, and which wavelengths will give rise to a defect mode at the location of a defect within the crystal.

The wavelength-tunable resonant cavity 210 may function as a resonant defect cavity in a photonic crystal, in addition to functioning as a Fabry-Perot resonant cavity (as described previously in relation to the resonant cavity 110 FIGS. 1A and 1B). A photonic bandgap may exist over certain frequencies in the direction orthogonal to the planes of the thin films. However, at least one defect mode within the bandgap may be generated as a result of the discontinuity of the periodicity in refractive index generated by the wavelength-tunable resonant cavity 210. The frequency of radiation corresponding to this defect mode may be amplified within the interior of the wavelength-tunable resonant cavity 210.

The distance D between the upper material layer 211 and the lower material layer 214 can be changed or adjusted in the same manner as disclosed in relation to the first exemplary embodiment. This will effectively alter the dimensions of the wavelength-tunable resonant cavity 210, thereby shifting the frequency associated with the defect modes by a factor 6, as shown in FIG. 2B. In this way, the resonant cavity 210 may be tuned to amplify the precise wavelength of the excitation radiation in the same way as the resonant cavity 110 of the first exemplary embodiment.

The wavelength of the excitation radiation may be selected to be outside the bandgap associated with the photonic crystals of the upper material layer 211 and the lower material layer 214. When the wavelength is outside the photonic bandgap of the Bragg mirrors, the excitation radiation may still be amplified within the resonant cavity 210 by the Fabry-Perot effect, and the device may function similar to the radiation amplifying structure 100 (FIGS. 1A and 1B).

Figure 4A:
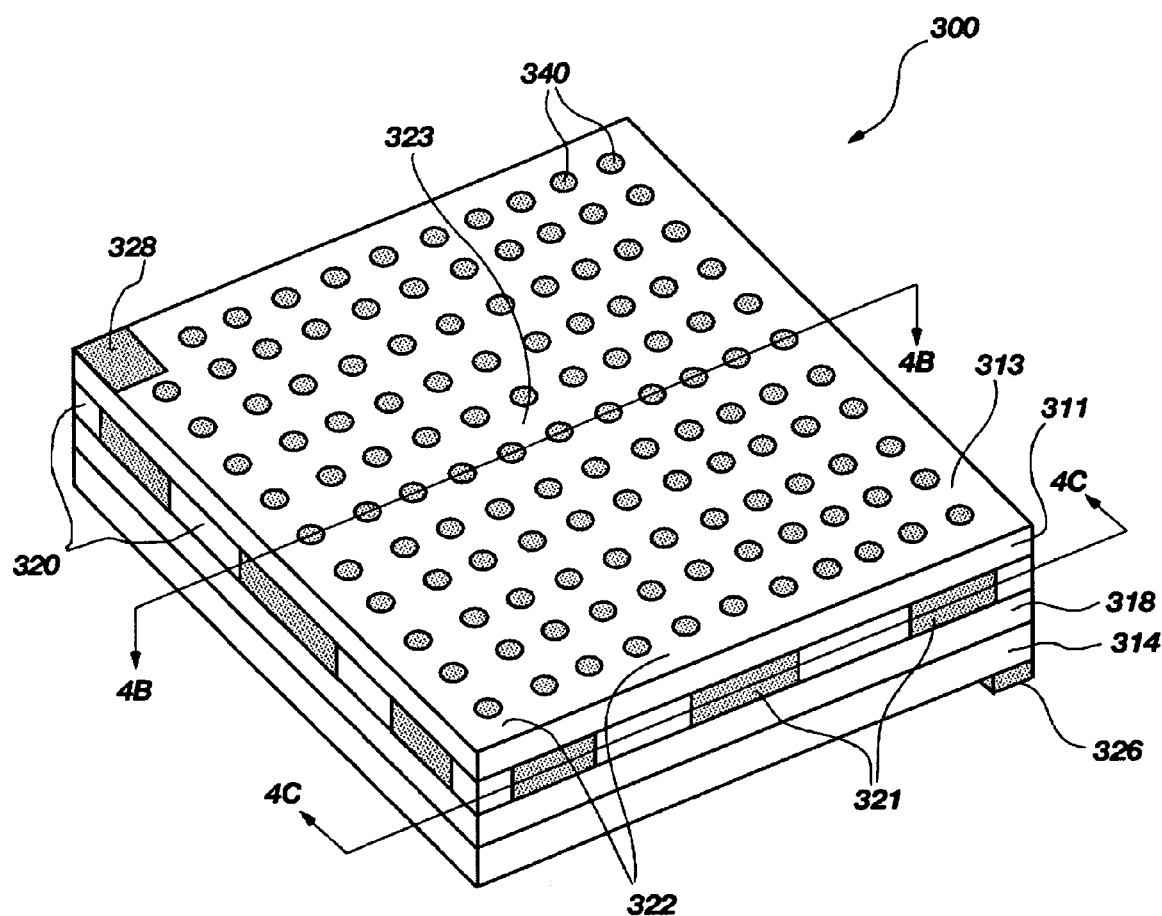
FIG. 4A is a perspective view of an exemplary apparatus of the invention comprising a deflectable membrane and photonic crystals.
Figure 4B:
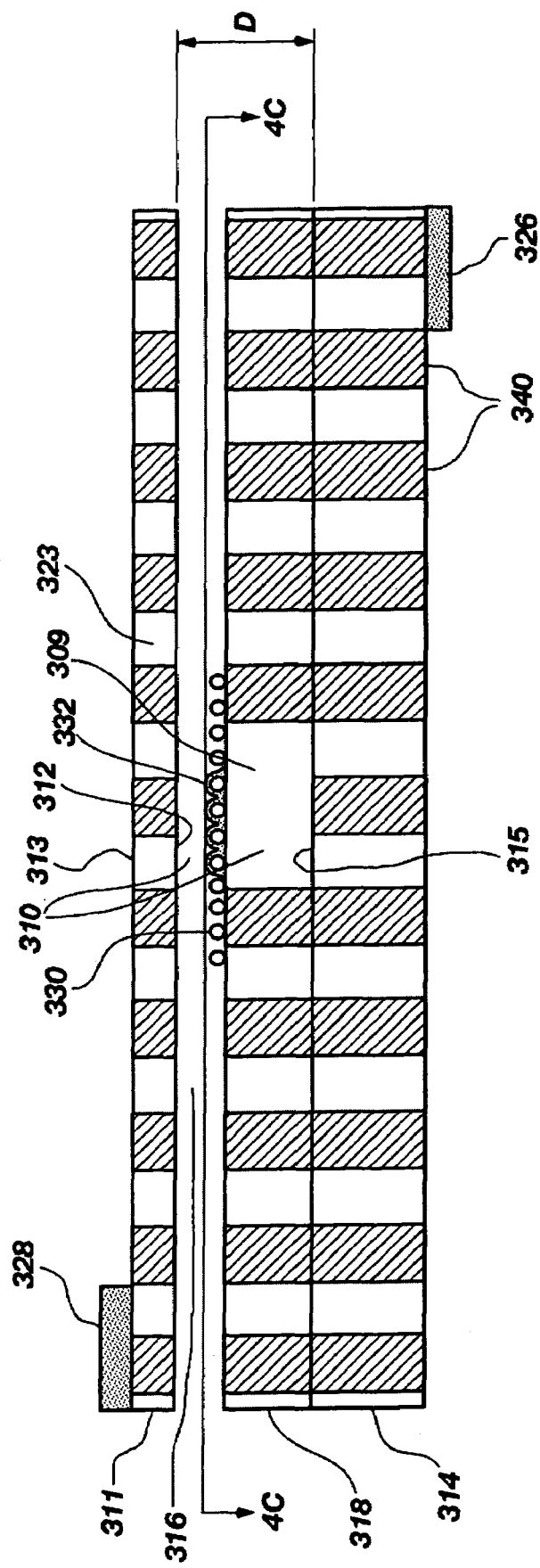
FIG. 4B is a cross-sectional view of the apparatus of FIG. 4A taken along line 4B-4B.

A third exemplary embodiment of the invention is illustrated in FIGS. 4A-4E. A wavelength-tunable radiation amplifying structure 300 may include an upper material layer 311 and a lower material layer 314 separated by a distance D (FIG. 4B). Insulating support members 320 may be disposed between at least a portion of the upper material layer 311 and at least a portion of the lower material layer 314, and an air gap 316 may be provided between the remaining portions. A resonant cavity 310 is defined between the upper material layer 311 and the lower material layer 314, and may include at least a portion of the air gap 316. A Raman signal-enhancing structure 330 may be disposed between the upper material layer 311 and the lower material layer 314 within the resonant cavity 310. A cavity layer 318 also may be disposed between the upper material layer 311 and the lower material layer 314.

Figure 4C:
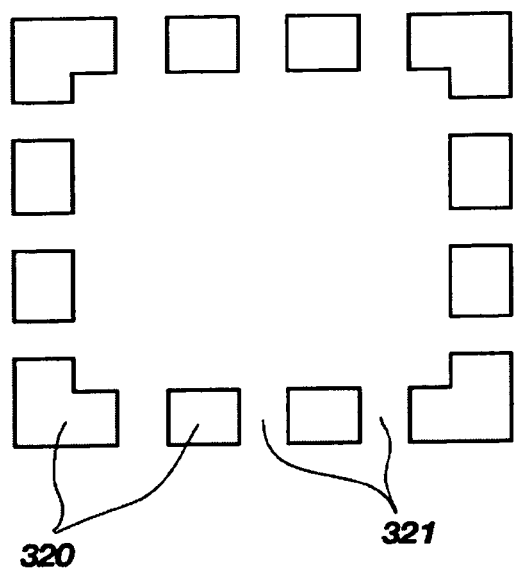
FIG. 4C is a cross-sectional view of the apparatus of FIG. 4A taken along line 4C-4C illustrating side ports that allow for analyte entry into the area proximate the wavelength-tunable resonant cavity.

The upper material layer 311 may be formed as a thin membrane that is supported above the lower material layer 314 by the cavity layer 318 and the insulating support members 320 (FIGS. 4A and 4C). The upper material layer 311 may include a peripheral first portion 322 (FIG. 4A), which may be attached to the insulating support members 320. The upper material layer 311 also may include a deflectable center second portion 323. The second portion 323 of the upper material layer 311 may include a lower surface 312 (FIG. 4B) and an upper surface 313 that are generally parallel to each other. The lower material layer 314 may include a face 315 opposing the lower surface 312 of the upper material layer 311 and may be separated therefrom by a distance D.

The outer periphery of the lower surface 312 of the upper material layer 311 may be attached to a first end of each of twelve insulating support structures 320, which are attached on a second end thereof to the cavity layer 318. The insulating support structures 320 may be formed from any dielectric or nonconductive material such as, for example, silicon dioxide. Ports 321 (FIG. 4A) are defined between the twelve insulating support structures 320. An analyte 332 may enter into or be placed within the interior of the radiation amplifying structure 300 and into the gap 316 between upper material layer 311 and cavity layer 318 through ports 321. Alternatively, fewer insulating support structures 320, or support structures having different shapes, could be used to support upper material layer 311 above cavity layer 318 and lower material layer 314.

Upper material layer 311 and lower material layer 314 each may include a two-dimensional photonic crystal having columns or rods 340 of a first material periodically dispersed within a matrix of a second material. The columns 340 may have a diameter that is approximately equal to a fraction of the wavelength of the excitation radiation. In addition, the columns 340 may be spaced approximately equidistant from one another by a distance similar to the diameter of the columns 340.

Figure 4D:
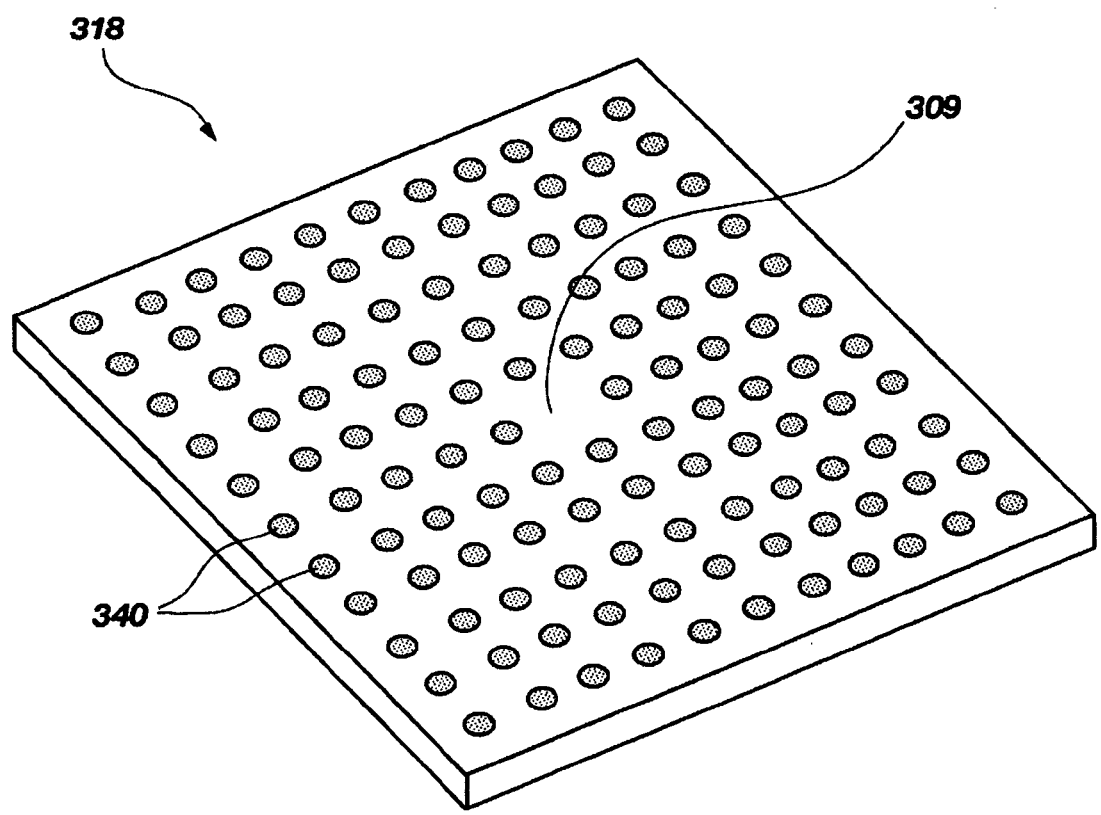
FIG. 4D is a perspective view of the cavity layer of the apparatus of FIG. 4A.

Cavity layer 318 may also include a two-dimensional photonic crystal, similar to those of the upper material layer 311 and the lower material layer 314, having columns 340 of a first material periodically dispersed within a matrix of a second material. However, one column in the center of the cavity layer 318 is missing, creating a defect cavity 309, as shown in FIG. 4D. Alternatively, defect cavity 309 could be formed as a void or a spatially confined area of a different material such as glass or epoxy. The wavelength-tunable resonant cavity 310 may include the defect cavity 309 and at least a portion of the air gap 316.

Examples of suitable materials for the columns 340 and the matrix in which they are disposed include, but are not limited to: GaAs and AlGaAs; AlGaAs columns within an AlGaAs matrix having different atomic percents of Al and Ga; GaN and GaAlN; and GaInAsP and InP. In practice, virtually any two conductive or semiconductive materials that have different refractive indices may be used.

An upper electrical contact 328 may be disposed on the upper surface of upper material layer 311. A lower electrical contact 326 may be disposed on the lower surface of lower material layer 314. The insulating support structures 320 may be formed from any dielectric or nonconductive material such as, for example, silicon dioxide. The lower electrical contact 326 and the upper electrical contact 328 may be formed from any conductive material including, but not limited to, gold, copper, platinum, silver, or any other conductive metal or alloy.

At least a portion of a Raman signal-enhancing structure 330, similar to the Raman signal-enhancing structure 130 of FIG. 1, may be disposed within the wavelength-tunable resonant cavity 310. The representative Raman signal-enhancing structure 330 illustrated in FIG. 4B includes an array of metallic nanospheres preferably having a diameter less than about 20 nanometers. The Raman signal-enhancing structure 330 may be positioned anywhere within the portion of air gap 316 proximate the defect cavity 309 of cavity layer 318.

All features or structures of the radiation amplifying structure 300, including the upper material layer 311, the lower material layer 314, the cavity layer 318, the insulating support structures 320, the upper electrical contact 328, the lower electrical contact 326, and the Raman signal-enhancing structure 330 may all be formed using known microelectronic fabrication techniques similar to those discussed above in relation to the first and second exemplary embodiments.

Figure 4E:
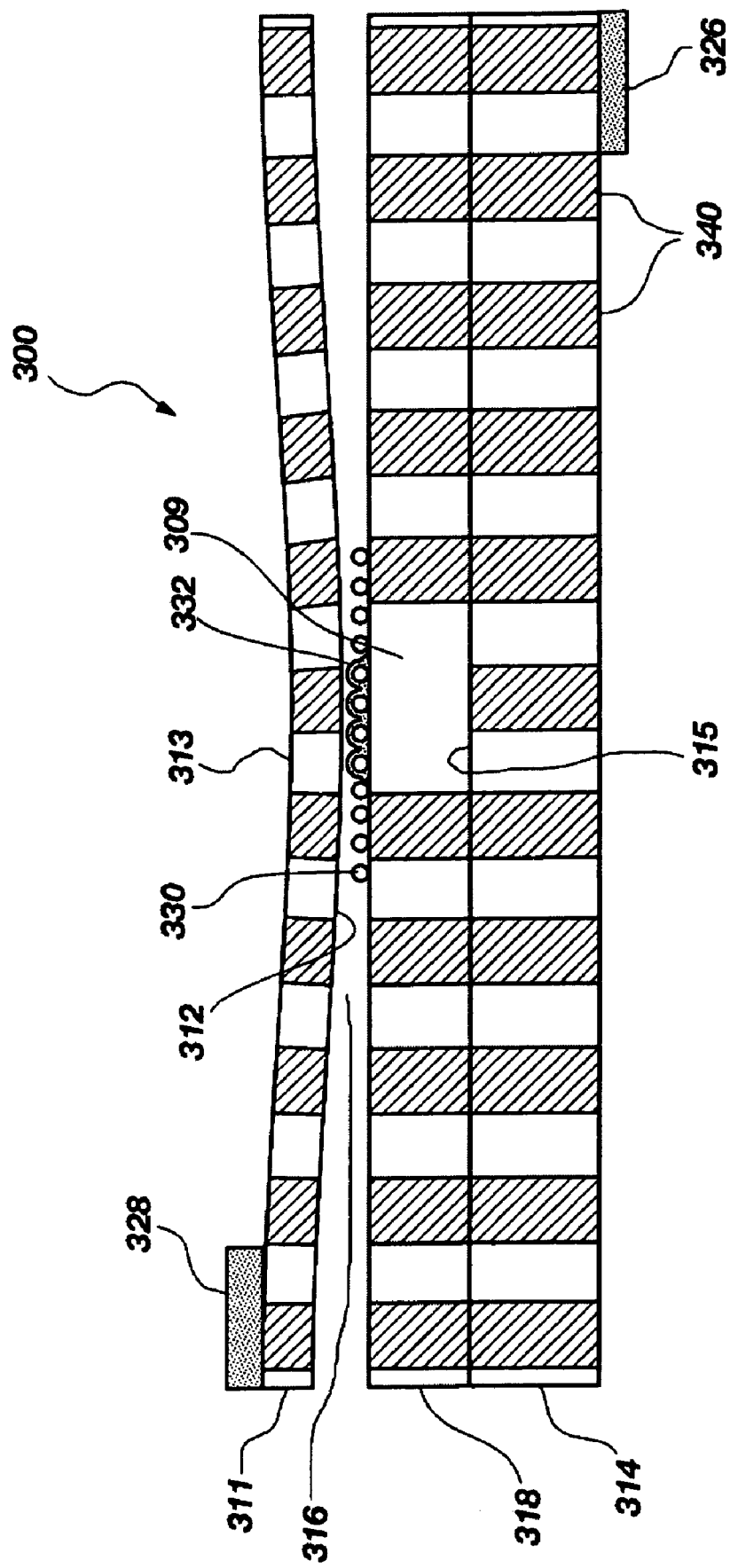
FIG. 4E is a modification of FIG. 4B illustrating the deflectable membrane in a deflected state.

The operation of the radiation amplifying structure 300 is best described with reference to FIGS. 4B and 4E. The upper material layer 311 and the lower material layer 314 may function as the material layers of a Fabry-Perot resonator. When excitation radiation impinges on the upper surface 313 of upper material layer 311, some of the radiation will pass through the upper material layer 311 into the resonant cavity where it may be internally reflected either constructively or destructively as described previously in relation to the radiation amplifying structure 100 of FIGS. 1A and 1B.

When the excitation radiation that is reflected inside the resonant cavity 310 interferes destructively and is not amplified, a voltage may be applied between the lower electrical contact 326 and the upper electrical contact 328 to tune the resonant cavity. The lower electrical contact 326 and the upper electrical contact 328 may be electrically continuous with the upper material layer 311 and the lower material layer 314 respectively (which may be formed from various semiconductive materials as described above). As a result, opposite charges may accumulate within the upper material layer 311 and the lower material layer 314. Because the charges are opposite, an attractive electrostatic force is applied between the upper material layer 311 and the lower material layer 314, causing the deflectable central second portion 323 of the thin upper material layer 311 to deflect downwards at the center thereof towards lower material layer 314, as shown in FIG. 4E. In this manner, the voltage may be adjusted and the distance D changed until the excitation radiation is amplified within the resonant cavity 310. If the excitation radiation source includes a wavelength-tunable laser, both the wavelength of the laser and the resonating frequency of the cavity can be adjusted providing a greater range of tunability.

The upper material layer 311 should be sufficiently thin to deflect towards the cavity layer 118 and the lower material layer 114 when a voltage is applied between the upper electrical contact 328 and the lower electrical contact 326. Alternatively, a portion of the upper material layer 311 surrounding the center portion of upper material layer above defect cavity 309 may be formed from a material having a lower Young's modulus than the previously discussed semiconductor materials, such as, for example, a polymer material, to provide a greater deflection of the upper material layer 311 (a greater change in the distance D) for a given applied voltage.

Some of the photons of the amplified excitation radiation within the resonant cavity may be scattered inelastically by the analyte 332 as Stokes and Anti-Stokes Raman radiation, which may be detected by a detector. The Stokes and Anti-Stokes radiation may be scattered in all directions and may be detected at any angle relative to the incident direction of the excitation radiation. However, the scattered Raman signal is typically detected from a direction orthogonal to the incident excitation radiation in SERS systems to minimize the detected signal from excitation radiation not scattered by the analyte.

Because the lower material layer 314, the upper material layer 311 and the cavity layer 318 each are include two-dimensional photonic crystals exhibiting periodicity in refractive index in the directions parallel to the planes of each layer, each layer may exhibit a photonic band gap in any such direction. If the lower material layer 314, the upper material layer 311, and the cavity layer 318 exhibit a photonic bandgap that includes the wavelength or frequency of the excitation radiation, the excitation radiation may be locally confined to the area in the vicinity of the defect cavity 309, and the portion of the analyte 332 adjacent thereto, thereby further increasing the intensity of the excitation radiation in the vicinity of the resonant cavity 310.

In addition, the cavity layer 318 may exhibit defect modes within the photonic bandgap that are associated with the defect cavity 309. If excitation radiation having a wavelength that corresponds to the defect mode is incident on a side of the structure instead of on the top or bottom of the structure, the radiation may resonate, increasing the intensity thereof, in the vicinity of the defect cavity 309.

The lower material layer 314 and the upper material layer 311 of the radiation amplifying structure 300 shown in FIG. 4 alternatively may include three-dimensional photonic crystals, which may include small spheres or other spatially confined areas of a first material having a first refractive index periodically dispersed within a matrix of a second material having a second, different, refractive index. Three-dimensional photonic crystals may be formed by stacking two-dimensional photonic crystals in an offset configuration. For example, the columns of one layer may be located directly above a matrix region of the layer below. Multiple layers may be stacked to create a three-dimensional photonic crystal structure. Such three-dimensional photonic crystals exhibit periodicity in refractive index in all three dimensions within the crystal.

Cavity layer 318 could be employed in the radiation amplifying structures 100 and 200 (FIGS. 1 and 3 respectively) to increase the efficiency thereof. For example, referring to the Radiation amplifying structure 200 shown in FIG. 3, the cavity layer 318 could be disposed in the air gap 216 between upper material layer 211 and lower material layer 214, and the SERS signal-enhancing structure 230 and analyte 232 could be disposed above the cavity layer.

Alternatively, upper material layer 311 and lower material layer 314 may include a one-dimensional photonic crystal such as a Bragg mirror. The upper material layer 311 and the lower material layer 314 may include a three-dimensional photonic crystal formed by dispersing small spheres or spatially confined areas of a first material having a first refractive index periodically within a matrix of a second material having a second refractive index. The upper material layer 311 and the lower material layer 314 also may include material layers that do not include photonic crystals, such as those discussed in relation to the radiation amplifying structure 100. In addition, radiation amplifying structure 300 may be formed without the cavity layer 318.

In some of these alternative embodiments, the upper material layer 311 and the lower material layer 314 could be configured to exhibit periodicity in refractive index in the vertical direction, or the direction parallel to the incident excitation radiation, thereby creating a photonic bandgap over certain wavelengths. In such a case, the wavelength-tunable resonant cavity 310 (or any other discontinuity in the periodicity in refractive index) may generate a defect mode.

Changing the distance D between the upper material layer 311 and the defect layer 318 would effectively vary the dimensions of the defect cavity 309, and may cause the wavelength associated with the defect mode to shift, thereby tuning the cavity in the same fashion as in the described previously herein. In such a situation, the device may function similarly to the Radiation amplifying structure 200 of the second exemplary embodiment, which includes one-dimensional photonic crystal Bragg mirrors.

Figure 5:
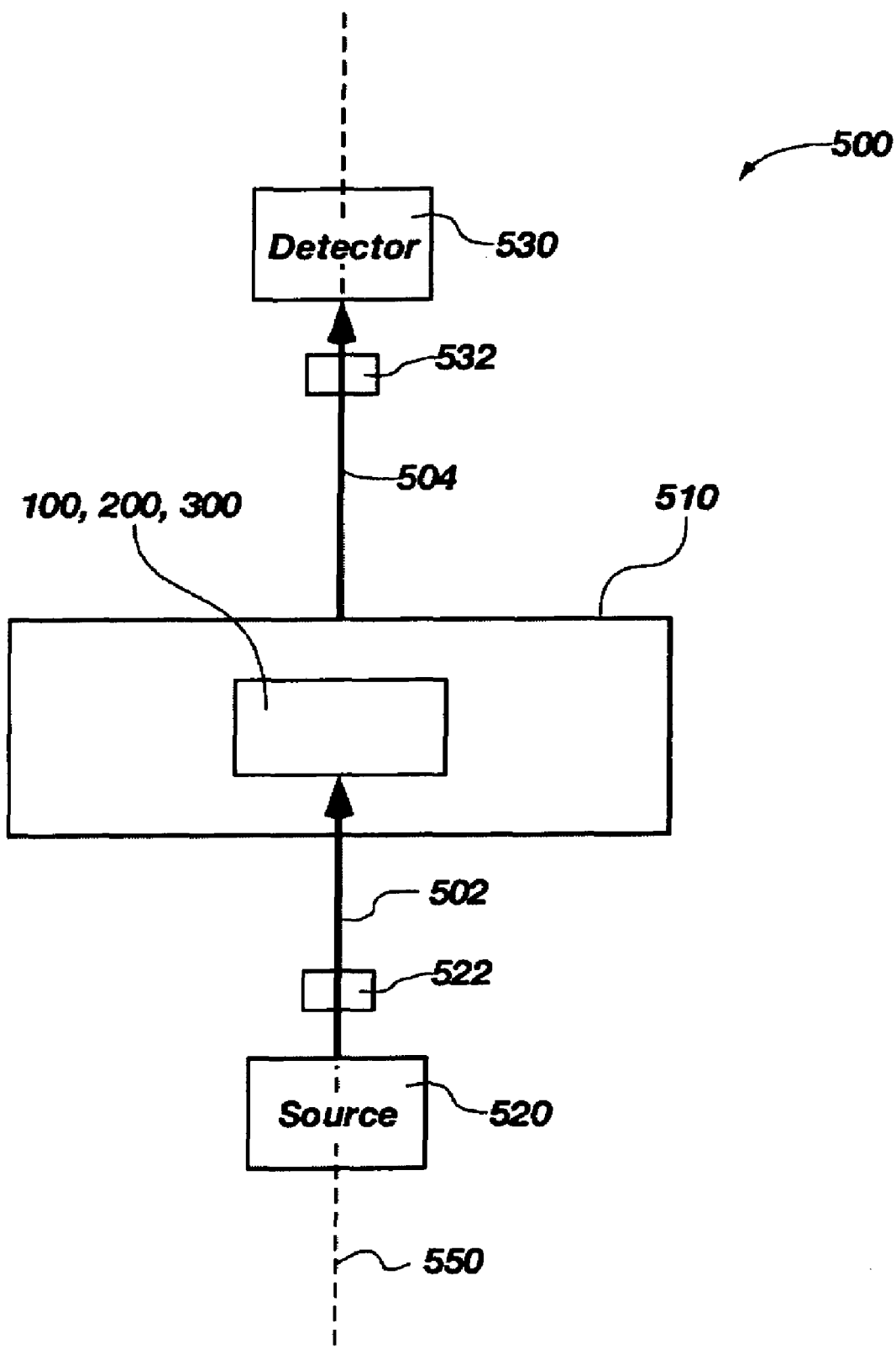
FIG. 5 is a schematic illustration of an exemplary SERS system that may employ any one of the radiation amplifying structures of FIGS. 1, 3, and 4.

Referring to FIG. 5, an exemplary SERS system 500 may include a SERS sample or analyte stage 510, an excitation radiation source 520, and a detector 530. The analyte stage 510 includes any one of the excitation radiation amplifying structures 100, 200, and 300 (FIGS. 1, 2, and 4 respectively). The SERS system 500 may also include various optical components 522 between the excitation radiation source 520 and the analyte stage 510, and various optical components 532 between the analyte stage 510 and the detector 530.

The excitation radiation source 520 may be any suitable source configured for emitting radiation of the desired wavelength and may be capable of emitting a tunable wavelength. As an example, commercially available semi-conductor lasers, helium-neon lasers, carbon dioxide lasers, light emitting diodes, incandescent lamps, and many other known radiation emitting sources may be used as the excitation radiation source 520. The wavelengths that are emitted by the excitation radiation source 520 employed in the SERS system 500 of the present invention may be any suitable wavelength for properly analyzing the analyte contained within the excitation radiation amplifying structure of the analyte stage 510. As an example, a representative range for the wavelengths that may be emitted by the excitation radiation source 520 includes wavelengths from about 350 nm to about 1000 nm.

The excitation radiation 502 from the source 520 may be delivered either directly from the source 520 to the analyte stage 510 and radiation amplifying structure. Alternatively, collimation, filtration, and subsequent focusing of excitation radiation 502 with optical components 522 may be performed before the excitation radiation 502 impinges on a surface of the radiation amplifying structure of the analyte stage 510. The radiation amplifying structure of the analyte stage may be oriented in any direction relative to the impinging excitation radiation 502 that allows the excitation radiation to be amplified within the structure, but is preferably oriented so that the excitation radiation impinges on either a top layer or bottom layer of the excitation radiation amplifying structure in a direction perpendicular thereto (i.e., in the direction L shown in FIG. 1B).

The radiation amplifying structure of the analyte stage 510 will amplify the excitation radiation 502 within a resonant cavity (i.e., 110, 210, and 310) as discussed previously with respect to each of the embodiments of the invention. The amplified excitation radiation will impinge on both the Raman signal-enhancing structure and the analyte disposed adjacent the Raman signal-enhancing structure near (or within) the resonant cavity of the radiation amplifying structure. The irradiation of the Raman signal-enhancing structure by the amplified excitation radiation produces a surface enhancement effect therein. In other words, irradiation of the Raman signal-enhancing structure by amplified excitation radiation 502 may produce a strong electromagnetic field near the Raman signal-enhancing structure. The analyte adjacent the portion of the Raman signal-enhancing structure that is being irradiated by amplified excitation radiation 502, in turn, experiences a very strong electromagnetic field. At least a portion of the amplified radiation may impinge on the analyte and may be inelastically scattered as Stokes or anti-Stokes radiation (or both) to produce Raman scattered photons 504. The electromagnetic field enhances the intensity of the signal produced by Raman photons 504 scattered by the analyte. Because the intensity of the Raman photons 504 scattered by the analyte is, in part, proportional to the square of the electromagnetic field experienced by the analyte, the enhancement effect from the Raman signal-enhancing structure may increase the intensity of the signal of the Raman scattered photons 504 by as much as $10^{14}$.

The Raman scattered photons 504 scattered by the analyte or sample may be collimated, filtered, or focused with optical components 532. For example, a filter or a plurality of filters may be employed, either included with the structure of the detector 530, or as a separate unit that is configured to filter the wavelength of the excitation radiation 502 from the excitation radiation source 520, thus, allowing only the Raman scattered photons 504 to be received by the detector 530.

The detector 530 receives and detects the Raman scattered photons 504 and may include a monochromator (or any other suitable device for determining the wavelength of the Raman scattered photons 504) and a device such as, for example, a photomultiplier for determining the quantity or number of the emitted Raman scattered photons (intensity). If desired, the detector 530 may also be positioned on the same side of the analyte stage 510 as the excitation radiation source 520 to receive Raman scattered photons 504.

Ideally, the Raman scattered photons 504 are isotropic, being scattered in all directions relative to the analyte stage 510. Thus, the position of detector 530 relative to the analyte stage 510 is not particularly important. However, the detector 530 may be positioned at, for example, an angle of 90° relative to the direction of the incident excitation radiation 502 to minimize the intensity of the incident excitation radiation 502 that may be incident on the detector 530.

Figure 6:
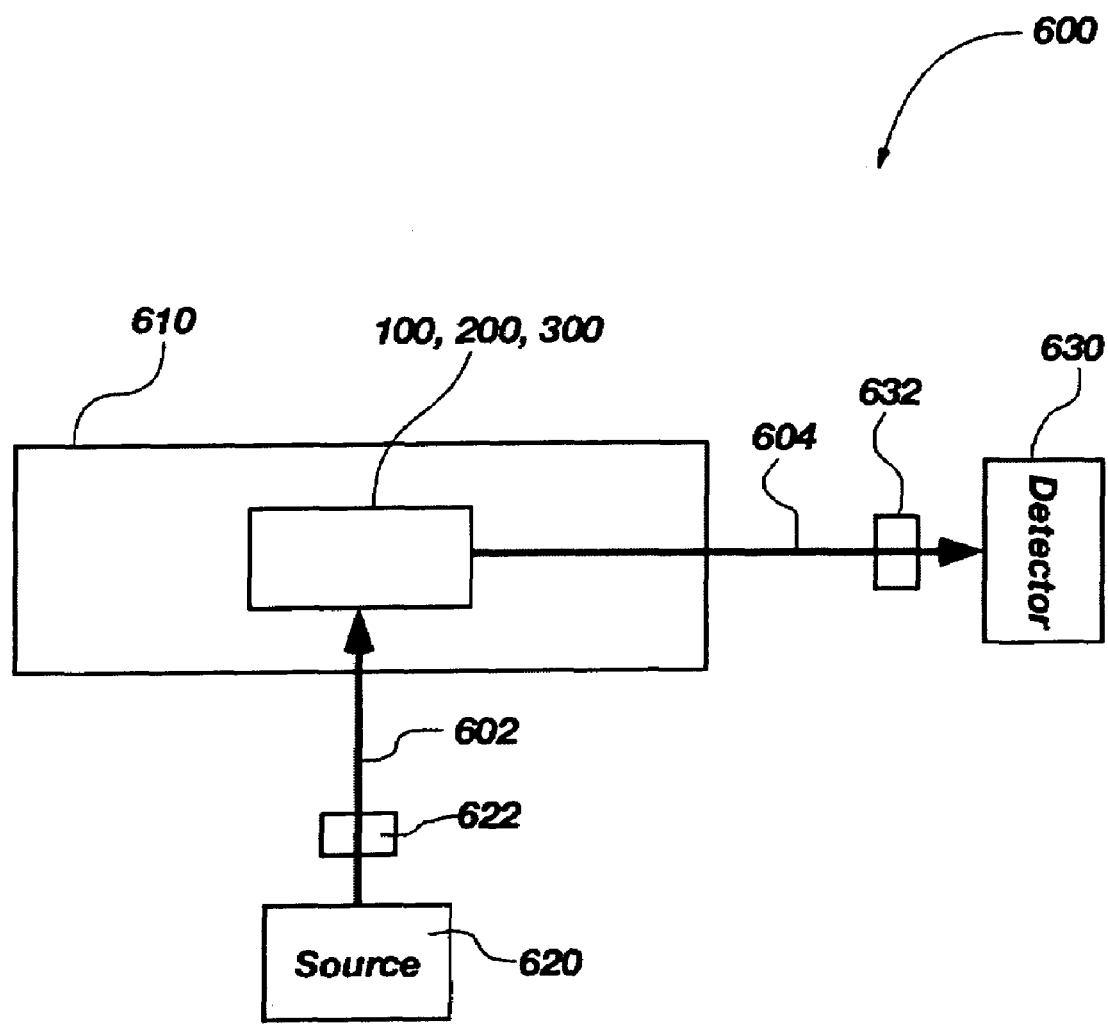
FIG. 6 is a schematic illustration of an exemplary SERS system that may employ any one of the radiation amplifying structures of FIGS. 1, 3, and 4, wherein the detector is oriented 90 degrees relative to the direction of the incident radiation.

As shown in FIG. 6, an exemplary SERS system 600 includes a SERS sample or analyte stage 610, an excitation radiation source 620, and a detector 630. The SERS sample or analyte stage 610 includes any one of the excitation radiation amplifying structures 100, 200, and 300 disclosed herein. The SERS system 600 may also include various optical components 622 between the excitation radiation source 620 and the analyte stage 610, and various optical components 632 between the analyte stage 610 and the detector 630. In contrast to the SERS system 500 of FIG. 5, however, the detector 630 of the SERS system 600 is positioned at approximately an angle of 90° relative to the direction of the incident excitation radiation 602 to minimize the intensity of the incident excitation radiation 602 that may be incident on the detector 630.

The spectroscopic analysis systems 500 and 600 shown in FIGS. 5 and 6 are configured to perform SERS and include a Raman signal-enhancing structure and employ excitation radiation within the visible spectrum. The system could be configured to perform other types of spectroscopy, however, by using an excitation radiation source that emits radiation having a wavelength outside the visible spectrum, a radiation amplifying structure having a larger or smaller resonant cavity (i.e., having a distance D capable of amplifying the particular wavelength of the incident radiation), and an appropriate detector.

The analyte stages of the present invention may amplify the intensity of various wavelengths of excitation radiation provided by a source, such as a laser, in a spectroscopic system. By amplifying the intensity of the excitation radiation, a low-power radiation source may be used. Low-power radiation sources are smaller, portable, cost less, and are cheaper to operate than conventional high-power radiation sources typically used in spectroscopic systems. In addition, the strength of the detected Raman signal is proportional to the intensity of the incident excitation radiation. Therefore, a stronger signal from inelastically scattered radiation emitted from the excited analyte can be produced and detected when using the wavelength-tunable resonant cavities of the present invention in typical spectroscopic analysis systems with conventional excitation radiation sources. A stronger signal from inelastically scattered radiation emitted from the excited analyte also allows for more sensitive and accurate chemical analysis of the analyte, including its chemical state and physical properties. The radiation amplifying structures are also tunable, which allows the user to adjust the resonant modes of the structure to accommodate varying wavelengths of incident radiation, overcoming the difficulties associated with manufacturing resonant cavities to resonate precise wavelengths.

Although the foregoing description contains many specifics, these are not to be construed as limiting the scope of the invention, but merely as providing certain exemplary embodiments. Similarly, other embodiments of the invention may be devised which do not depart from the spirit or scope of the present invention. The scope of the invention is, therefore, indicated and limited only by the appended claims and their legal equivalents, rather than by the foregoing description. All additions, deletions, and modifications to the invention, as disclosed herein, which fall within the meaning and scope of the claims are encompassed by the present invention.

What is claimed is:

1. A wavelength-tunable excitation radiation amplifying structure comprising:
    an insulating support structure;
    a first material layer attached to the support structure having a face;
    a second material layer having a first portion attached to the support structure and a second portion having a first surface and a second surface, the second surface being generally parallel to the first surface, the second surface opposing the face of the first material layer and separated therefrom by a distance;
    means for displacing the second portion of the second material layer relative to the face of the first material layer to change the distance therebetween; and
    at least a portion of a Raman signal-enhancing structure disposed between the face of the first material layer and the second surface of the second portion of the second material layer.

2. The radiation amplifying structure of claim 1, wherein the second material layer further comprises a cantilever arm extending between the first portion and the second portion thereof.

3. The radiation amplifying structure of claim 1, wherein the second material layer comprises a thin layer that enables the second portion of the second material layer to be deflected relative to the first material layer.

4. The radiation amplifying structure of claim 1, wherein the means for displacing the second portion of the second material layer relative to the face of the first material layer to change the distance therebetween comprise:
    a first electrical contact disposed on the first material layer; and
    a second electrical contact disposed on the second material layer, whereby a voltage applied between the first electrical contact and the second electrical contact causes the distance between the first material layer and the second portion of the second material layer to change.

5. The radiation amplifying structure of claim 1, further comprising a two-dimensional (2-D) photonic crystal disposed between the face of the first material layer and the second surface of the second portion of the second material layer, the 2-D photonic crystal having a defect therein proximate the Raman signal-enhancing structure.

6. The radiation amplifying structure of claim 5, further comprising ports therein extending between the at least a portion of the Raman signal enhancing structure and the exterior of the radiation amplifying structure.

7. The radiation amplifying structure of claim 1, wherein the first material layer and the second material layer comprise Bragg mirrors.

8. The radiation amplifying structure of claim 1, wherein the first material layer and the second material layer comprise a doped semiconductor material.

9. The radiation amplifying structure of claim 1, wherein the Raman signal-enhancing structure comprises a metallic nanostructure.

10. The radiation amplifying structure of claim 6, wherein the metallic nanostructure comprises at least one wire having a diameter less than about 20 nanometers.

11. A wavelength-tunable excitation radiation amplifying structure comprising:
    an insulating support structure;
    a first material layer attached to the insulating support structure having a face;
    a second material layer having a first portion attached to the insulating support structure and a second portion having a first surface and a second surface, the second surface being generally parallel to the first surface, the second surface opposing the face of the first material layer and separated therefrom by a distance;
    a first electrical contact disposed on the first material layer;
    a second electrical contact disposed on the second material layer, whereby a voltage applied between the first electrical contact and the second electrical contact causes the distance to between the first material layer and the second portion of the second material layer to change; and
    at least a portion of a Raman signal-enhancing structure disposed between the face of the first material layer and the second surface of the second portion of the second material layer.

12. The radiation amplifying structure of claim 11, wherein the second material layer further comprises a cantilever arm extending between the first portion and the second portion thereof.

13. The radiation amplifying structure of claim 11, wherein the second material layer comprises a thin layer that enables the second portion of the second material layer to be deflected relative to the first material layer.

14. The radiation amplifying structure of claim 11, further comprising a two-dimensional (2-D) photonic crystal disposed between the face of the first material layer and the second surface of the second portion of the second material layer, the 2-D photonic crystal having a defect therein proximate the Raman signal-enhancing structure.

15. The radiation amplifying structure of claim 14, wherein the first material layer and the second material layer comprise Bragg mirrors.

16. The radiation amplifying structure of claim 11, wherein the first material layer and the second material layer comprise Bragg mirrors.

17. The radiation amplifying structure of claim 11, wherein the first material layer and the second material layer comprise a doped semiconductor material.

18. The radiation amplifying structure of claim 11, wherein the Raman signal-enhancing structure comprises a metallic nanostructure.

19. The radiation amplifying structure of claim 18, wherein the metallic nanostructure comprises at least one sphere having a diameter less than about 20 nanometers.

20. A spectroscopic analysis system comprising:
a radiation source for emitting excitation radiation;
a support structure;
a first material layer attached to the support structure having a face;
a second material layer having a first portion attached to the support structure and a second portion having a first surface and a second surface, the second surface being generally parallel to the first surface, the second surface opposing the face of the first material layer and separated therefrom by a distance;
means for displacing the second portion of the second material layer relative to the first material layer to change the distance therebetween;
at least a portion of a Raman signal-enhancing structure disposed between the face of the first material layer and the second surface of the second portion of the second material layer; and
a detector configured to receive radiation emitted from an analyte when the analyte is subjected to excitation radiation emitted from the source.

21. The spectroscopic analysis system of claim 20, wherein the second material layer further comprises a cantilever arm extending between the first portion and the second portion thereof.

22. The spectroscopic analysis system of claim 20, wherein the second material layer comprises a thin layer that enables the second portion of the second material layer to be deflected relative to the first material layer.

23. The spectroscopic analysis system of claim 20, wherein the means for displacing the second portion of the second material layer relative to the face of the first material layer to change the distance therebetween comprise:
a first electrical contact disposed on the first material layer;
a second electrical contact disposed on the second material layer, whereby a voltage applied between the first electrical contact and the second electrical contact causes the distance to between the first material layer and the second portion of the second material layer to change.

24. The spectroscopic analysis system of claim 20, further comprising a two-dimensional (2-D) photonic crystal disposed between the face of the first material layer and the second surface of the second portion of the second material layer, the 2-D photonic crystal having a defect therein.

25. The spectroscopic analysis system of claim 24, further comprising ports therein extending between the at least a portion of the Raman signal-enhancing structure and the exterior of the structure.

26. The spectroscopic analysis system of claim 20, wherein the first material layer and the second material layer comprise Bragg mirrors.

27. The spectroscopic analysis system of claim 20, wherein the first material layer and the second material layer comprise a doped semiconductor material.

28. The spectroscopic analysis system of claim 20, wherein the excitation radiation amplifying structure further comprises a Raman signal-enhancing structure.

29. The spectroscopic analysis system of claim 28, wherein the Raman signal-enhancing structure comprises a metal selected from the group consisting of Au, Ag, Cu, Na, K, Cr, Al, and Li.

30. The spectroscopic analysis system of claim 28, wherein the Raman signal-enhancing structure comprises a metallic nanostructure.

31. The spectroscopic analysis system of claim 30, wherein the metallic nanostructure comprises at least one vertical column having a diameter less than about 20 nanometers.

32. The spectroscopic analysis system of claim 20, wherein the excitation radiation has a wavelength between about 350 nanometers and about 1000 nanometers.

33. The spectroscopic analysis system of claim 20, wherein the detector is configured to detect radiation emitted from the analyte in a direction substantially perpendicular to the direction of the excitation radiation.

34. The spectroscopic analysis system of claim 20, wherein the radiation source comprises a wavelength-tunable laser.

35. A method of performing surface enhanced Raman spectroscopy (SERS), comprising:
providing a wavelength-tunable excitation radiation amplifying structure comprising:
a support structure;
a first material layer attached to the support structure having a face;
a second material layer having a first portion attached to the support structure and a second portion having a first surface and a second surface, the second surface being generally parallel to the first surface, the second surface opposing the face of the first material layer and separated therefrom by a distance;
a first electrical contact disposed on the first material layer;
a second electrical contact disposed on the second material layer, whereby a voltage applied between the first electrical contact and the second electrical contact causes the distance between the first material layer and the second portion of the second material layer to change; and
at least a portion of a Raman signal-enhancing structure disposed between the face of the first material layer and the second surface of the second portion of the second material layer;
providing an analyte disposed proximate the Raman signal-enhancing structure;
irradiating a surface of the wavelength-tunable excitation radiation amplifying structure with excitation radiation; and
tuning the wavelength-tunable excitation radiation amplifying structure by applying a voltage between the first electrical contact and the second electrical contact and changing the voltage until the excitation radiation is amplified.

36. The method of claim 35, further comprising:
providing a detector positioned with respect to the structure to receive the radiation emitted from the analyte; and detecting radiation emitted from the analyte.

37. The method of claim 36, further comprising filtering the excitation radiation from being received by the detector.

38. The method of claim 35, further comprising:
selecting the wavelength of the excitation radiation to correspond to at least one of a resonance mode of a Fabry-Perot resonating cavity and a resonance mode associated with a defect in a photonic crystal.

39. A wavelength-tunable excitation radiation amplifying structure comprising:
a first material layer attached to an insulating support structure having a face;
a second material layer having a first portion attached to the support structure and a second portion having a surface opposing the face of the first material layer and separated therefrom by a distance;
means for displacing the second portion of the second material layer relative to the face of the first material layer to change the distance therebetween; and
a metallic nanostructure disposed between the face of the first material layer and the surface of the second portion of the second material layer.

40. The radiation amplifying structure of claim 39, wherein the first material layer and the second material layer comprise Bragg mirrors.

41. The radiation amplifying structure of claim 39, wherein the first material layer and the second material layer comprise a doped semiconductor material.

* * * * *

UNITED STATES PATENT AND TRADEMARK OFFICE
CERTIFICATE OF CORRECTION

PATENT NO. : 7,307,719 B2 Page 1 of 1
APPLICATION NO. : 10/941714
DATED : December 11, 2007
INVENTOR(S) : Shih-Yuan Wang et al.

It is certified that error appears in the above-identified patent and that said Letters Patent is hereby corrected as shown below:

On page 2, in field (56), under "US Patent Documents", in column 1, line 15,
delete "6,434,180 B1    8/2002           Cunningham" and
insert -- 6,343,180 B1    1/2002           Kim --, therefor.

Signed and Sealed this

Twenty-third Day of February, 2010

David J. Kappos
*Director of the United States Patent and Trademark Office*